United States Patent

Wild et al.

Patent Number: 5,457,108
Date of Patent: Oct. 10, 1995

[54] 5-OXO-DIBENZO[A,D]CYCLOHEPTA-1,4-DIENES

[75] Inventors: Hanno Wild; Jutta Hansen, both of Wuppertal; Jörg Lautz, Wuelfrath; Arnold Paessens, Haan, all of Germany

[73] Assignee: Bayer Aktiengesellschaft, Leverkusen, Germany

[21] Appl. No.: 122,279

[22] Filed: Sep. 17, 1993

[30] Foreign Application Priority Data

Sep. 25, 1992 [DE] Germany ............... 42 32 173.5

[51] Int. Cl.[6] ............... A61K 31/47; A61K 31/535; A61K 31/40; A61K 31/27; C07D 493/08; C07D 245/13; C07D 215/38; C07D 209/14; C07D 213/04; C07C 271/52; C07C 317/28; C07F 7/18

[52] U.S. Cl. ............... 514/237.8; 514/63; 514/311; 514/419; 514/456; 514/533; 514/616; 514/618; 514/680; 544/154; 546/156; 548/492; 549/408; 552/10; 556/441; 560/25; 560/27; 560/28; 560/32; 560/106; 560/251; 564/162; 564/185; 564/186; 564/309; 568/326

[58] Field of Search ............... 564/185, 196, 564/389, 162, 102, 186, 309; 560/27, 28, 32, 106, 251, 25; 514/63, 311, 419, 456, 533, 237.8, 616, 680; 544/154; 546/156; 548/492; 549/408; 552/10; 556/441; 568/326

[56] References Cited

U.S. PATENT DOCUMENTS

| | | | |
|---|---|---|---|
| 3,264,342 | 8/1966 | Schindler | 560/28 |
| 3,401,192 | 9/1968 | Kollonitsch et al. | 560/28 |
| 3,403,157 | 9/1968 | Humber et al. | 560/28 X |
| 3,436,402 | 4/1969 | Cassady et al. | 544/153 X |
| 3,513,201 | 5/1970 | Tischler et al. | 560/28 X |
| 3,660,389 | 5/1972 | Hucker et al. | 560/28 X |
| 3,911,017 | 10/1975 | Hardtmann | 564/387 |
| 3,992,445 | 11/1976 | Engelhardt | 564/387 X |
| 3,994,961 | 11/1976 | Houlihan et al. | 560/28 X |
| 4,062,840 | 12/1977 | Van Der Burg | 564/387 X |
| 4,317,910 | 3/1982 | Hauck et al. | 564/387 X |
| 4,596,892 | 6/1986 | Plummer | 564/387 |

OTHER PUBLICATIONS

Bulletin De La Societe Chimique De France 1960, pp. 400–405 Rigaudy et al.
Bioorg. Med. Chem. Lett. vol. 2, 541–546 (1992) Babine et al.
Journ. Med. Chem. vol. 35, 2525–2533 (1992) Tucker et al.
Journ. Med. Chem. vol. 34, 2305–2314 (1991) Huff.
Hansen, J. et al., (1988), EMBO Journal, vol. 7, No. 6, pp. 1785–1791.
Pauwels et al., Journal of Virological Methods vol. 20, (1988), pp. 309–321.

*Primary Examiner*—Floyd D. Higel
*Attorney, Agent, or Firm*—Sprung, Horn Kramer & Woods

[57] ABSTRACT

The invention relates to substituted 5-oxo-di-benzo[a,d]cyclohepta-1,4-dienes of the formula (I)

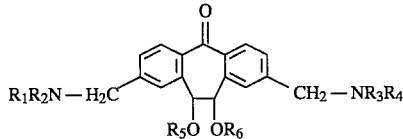

processes for their preparation and their use as retroviral agents.

6 Claims, No Drawings

5-OXO-DIBENZO[A,D]CYCLOHEPTA-1,4-DIENES

The invention relates to 5-oxo-dibenzo[a,d]cyclohepta-1,4-dienes, processes for their preparation and their use as retroviral agents.

Cis/trans- 10,11-dihydroxy-5-oxo-dibenzo [a,d]cyclohepta-1,4-diene and the corresponding diacetates are already known from the publication in Bull. Soc. Chim. Fr. (1960), 400.

The present invention now relates to substituted 5-oxo-dibenzo[a,d]cyclohepta-1,4-dienes of the general formula (I)

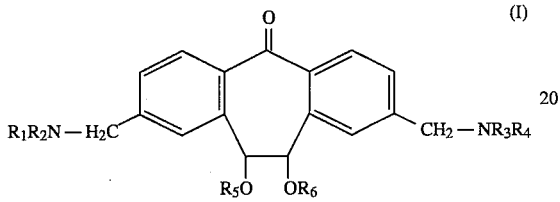

in which $R^1$ and $R^3$ are identical or different and represent an amino-protective group or represent a group of the formula $R^7$—CO—, in which $R^7$ denotes hydrogen, trifluoromethyl, or straight-chain or branched alkoxy having up to 8 carbon atoms or alkyl having up to 18 carbon atoms, which are optionally substituted identically or differently up to 2 times by aryl having 6 to 10 carbon atoms or pyridyl, or denotes aryl having 6 to 10 carbon atoms, which is optionally substituted by halogen, tri-fluoromethyl, trifluoromethoxy, or by straight-chain or branched alkyl having up to 8 carbon atoms, denotes cycloalkyl having 3 to 7 carbon atoms, or denotes quinolyl, quinolyl N-oxide, indolyl, pyridyl, morpholino or piperazinyl, or denotes a residue of the formula

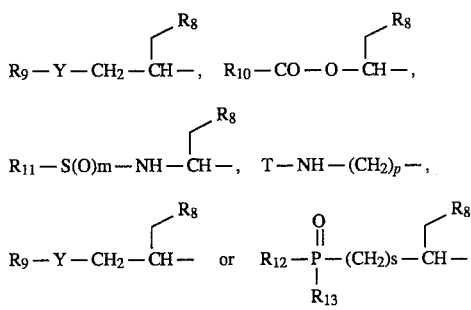

in which $R^8$ denotes phenyl or naphthyl, $R^9$, $R^{10}$ and $R^{11}$, independently of each other, denote straight-chain or branched alkyl having up to 14 carbon atoms, which is optionally substituted by phenyl or naphthyl, or denote aryl having 6 to 10 carbon atoms, which for its part is substituted by alkyl having up to 4 carbon atoms, or $R^{10}$ denotes a residue of the formula

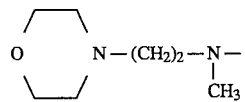

m denotes a number 0, 1 or 2,

T denotes morpholino or cyclohexyl, p denotes a number 1, 2 or 3,

Y and Y', independently of each other, represent CO— or $SO_2$—, $R^{12}$ and $R^{13}$ independently of each other, represent hydroxyl or alkoxy having up to 8 carbon atoms, s represents a number 1 or 2, $R^2$ and $R^4$ are identical or different and represent hydrogen, or straight-chain or branched alkyl having up to 8 carbon atoms, $R^5$ and $R^6$ are identical or different and represent hydrogen, or represent straight-chain or branched acyl or alkoxycarbonyl having in each case up to 8 carbon atoms, or represent a hydroxyl-protective group, and in the case that either $R^5$ or $R^6$ represents hydrogen, in the form of their hemiacetals and salts thereof.

Physiologically acceptable salts of the substituted 5-oxo-dibenzo[a,d]cyclohepta-1,4-dienes can be salts of the compounds according to the invention with mineral acids, carboxylic acids or sulphonic acids. Those which are particularly preferred are, e.g., salts with hydrochloric acid, hydrobromic acid, sulphuric acid, phosphoric acid, methanesulphonic acid, ethanesulphonic acid, toluenesulphonic acid, benzenesulphonic acid, nahphalenedisulphonic acid, acetic acid, propionic acid, lactic acid, tartaric acid, citric acid, fumaric acid, maleic acid or benzoic acid.

Salts with customary bases, such as, for example, alkali metal salts (e.g. sodium or potassium salts), alkaline earth metal salts ( e.g. calcium or magnesium salts ), or ammonium salts, derived from ammonia or organic amines, such as, for example, diethylamine, triethylamine, ethyldiisopropylamine, procaine, dibenzylamine, N-methylmorpholine, dehydroabietylamine, 1-ephenamine or methylpiperidine, can be mentioned as salts.

The compounds according to the invention can exist in stereoisomeric forms which either do (enantiomers) or do not (diastereomers) relate to each other as image and mirror image. The invention relates to both the antipodes and the racemic forms, as well as the diastereomeric mixtures. The racemic forms as well as the diastereomers can be separated in a known manner into the stereisomerically homogeneous components [cf. E. L. Eliel, Stereo-chemistry of Carbon Compounds, McGraw Hill, 1962].

Within the scope of the invention, amino-protective groups are the customary amino-protective groups which are used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichloroethoxycarbonyl, 2,2,2-trichloro-tertbutoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl.

In the residue of the formula (II),

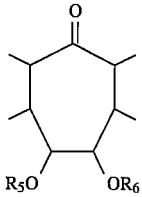
(II)

the groups —$OR^5$ and —$OR^6$ can be located in the cis- or trans-position in relation to each other or can be present as a cis/trans isomer mixture.

The definition of the hemiacetal form is illustrated by way of example by the residue of the formula (IIa):

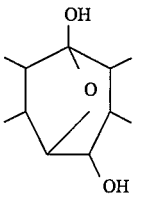
(IIa)

Hydroxyl-protective group generally represents trimethylsilyl, triethylsilyl, triisopropylsilyl, tert-butyldimethylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert-butoxycarbonyl, allyloxycarbonyl, 4methoxybenzyloxycarbonyl, formyl, acetyl, trichloroacetyl, 2,2,2-trichloroethoxycarbonyl, 2,4-dimethoxycarbonyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl or benzoyl.

Those which are preferred are trimethylsilyl, triethylsilyl, triisopropylsilyl, tert-butyl-dimethylsilyl, triphenylsilyl, benzyloxycarbonyl, 4-nitrobenzyloxycarbonyl, tert-butoxycarbonyl, allyloxycarbonyl, 4-methoxybenzyloxycarbonyl, formyl, acetyl and trichloroacetyl.

The compounds of the general formula (I) are preferred in which $R^1$ and $R^3$ are identical or different and represent benzyloxycarbonyl, 4-methoxybenzyloxycarbonyl, 4-nitrobenzyloxycarbonyl, tert-butoxycarbonyl, allyloxycarbonyl, 2-nitrobenzyloxycarbonyl, fluorenyl-9-methoxycarbonyl or 2,2,2-trifluoroacetyl, or represent a group of the formula $R^7$—CO—, $R^7$ denotes hydrogen, trifluoromethyl, or straight-chain or branched alkoxy having up to 4 carbon atoms or alkyl having up to 16 carbon atoms, which are optionally substituted identically or differently up to 2 times by phenyl, naphthyl or pyridyl, or denotes phenyl or naphthyl, which can be optionally substituted by fluorine, chlorine, trifluoromethyl, trifluoromethoxy, or by straight-chain or branched alkyl having up to 6 carbon atoms, denotes cyclopropyl, cyclopentyl, cyclohexyl, quinolyl, quinolyl N-oxide, indolyl, pyridyl, morpholino or piperazinyl, or denotes a residue of the formula

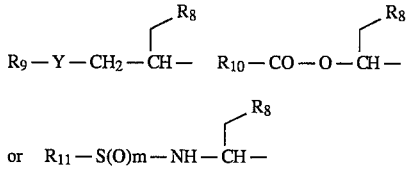

in which

Y denotes the CO or $SO_2$ group, $R^8$ denotes phenyl or naphthyl, $R^9$, $R^{10}$ and $R^{11}$, independently of each other, represent straight-chain or branched alkyl having up to 8 carbon atoms, tolyl, phenyl or naphthyl, or $R^{10}$ denotes a residue of the formula

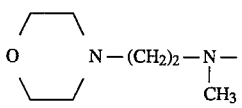

m denotes a number 1 or 2, $R^2$ and $R^4$ are identical or different and represent hydrogen, or straight-chain or branched alkyl having up to 6 carbon atoms, $R^5$ and $R^6$ are identical or different and represent hydrogen, or represent straight-chain or branched acyl or alkoxycarbonyl having in each case up to 6 carbon atoms or represent trimethylsilyl, triethylsilyl, triisopropylsilyl, tert-butyl-dimethylsilyl, triphenylsilyl, benzyloxycarbonyl, 4-nitrobenzyloxycarbonyl, tert-butoxycarbonyl, allyloxycarbonyl, 4-methoxybenzyloxycarbonyl, formyl, acetyl or trichloroacetyl, and in the case that either $R^5$ or $R^6$ represents hydrogen, in the form of their hemiacetals and salts thereof.

The compounds of the formula (I) are particularly preferred in which $R^1$ and $R^3$ are identical or different and represent benzyloxycarbonyl, 4-methoxybenzyloxycarbonyl, 4-nitrobenzyloxycarbonyl, tert-butoxycarbonyl, allyloxycarbonyl, 2-nitrobenzyloxycarbonyl, fluorenyl-9-methoxycarbonyl or 2,2,2-trifluoroacetyl, or represent a group of the formula $R^7$—CO—in which $R^7$ denotes hydrogen, trifluoromethyl, or straight-chain or branched alkoxy having up to 4 and alkyl having up to 14 carbon atoms, which are optionally substituted up to 2 times by phenyl, naphthyl or pyridyl, or denotes phenyl or naphthyl, which can optionally be substituted by fluorine, chlorine, trifluoromethyl, trifluoromethoxy, or by straight-chain or branched alkyl having up to 4 carbon atoms, denotes cyclopropyl, cyclopentyl, cyclohexyl, quinolyl, quinolyl N-oxide, indolyl, pyridyl, morpholino or piperazinyl, or denotes a residue of the formula

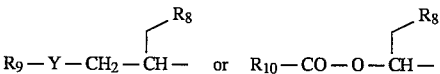

in which

Y denotes the CO or $SO_2$ group, $R^8$ denotes phenyl or naphthyl $R^9$ and $R^{10}$, independently of each other, represent straight-chain or branched alkyl having up to 4 carbon atoms, tolyl, phenyl or naphthyl, $R^{10}$ represents a residue of the formula,

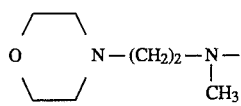

$R^2$ and $R^4$ are identical or different and represent hydrogen, or straight-chain or branched alkyl having up to 4 carbon atoms, $R^5$ and $R^6$ are identical or different and represent hydrogen, or represent straight-chain or branched acyl or alkoxycarbonyl having in each case up to 4 carbon atoms, or represent trimethylsilyl, triethylsilyl, triisopropylsilyl, tert-butyl-dimethylsilyl, triphenylsilyl, benzyloxycarbonyl, 4-nitrobenzyloxycarbonyl, tert-butoxycarbonyl, allyloxycarbonyl, 4-methoxybenzyloxycarbonyl, formyl, acetyl or trichloroacetyl, and in the case that either $R^5$ or $R^6$ represents hydrogen, in the form of their hemiacetals and salts thereof.

In addition, a process has been found for preparing the compounds of the general formula (I) according to the invention, characterised in that compounds of the general formula (III)

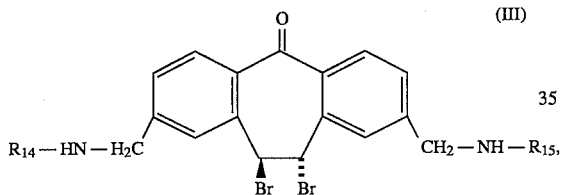

in which $R^{14}$ and $R^{15}$ are identical or different and represent an amino-protective group, preferably phenylmethoxycarbonyl, are first converted by reactions with carboxylic acids of the general formula (IV)

$$R^{16}\text{—}CO_2H \qquad (IV)$$

in which $R^{16}$ includes the respective range of meaning listed above for the substituents $R^5$ and $R^6$, with the exception of hydrogen, and in the presence of a corresponding salt, into the compounds of the general formulae (Ia) and (Ib)

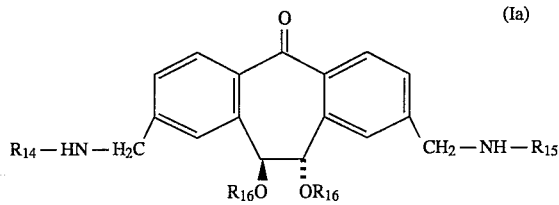

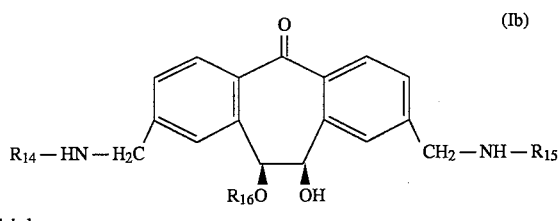

in which $R^{14}$ and $R^{15}$ have the abovementioned meaning, likewise has the abovementioned meaning, but preferably represents acetyl, the hydroxyl function ($R^5/R^6$=H) is subsequently liberated by hydrolysis, and in the case of the remaining substituents listed above under $R^1$ and $R^3$, the radicals $R^{14}$ and $R^{15}$ are first eliminated according to customary methods, preferably by hydrogenation, to liberate the amino function, and are reacted, in a last step, with compounds of the general formula (V)

$$R^{17}\text{—}CO_2H \qquad (V)$$

in which $R^{17}$ embraces the range of meaning of the above-listed substituents $R^1$ and $R^3$, in inert solvents, in the presence of a base and/or of an auxiliary compound, optionally with prior activation of the carboxylic acid function.

The process according to the invention can be illustrated, by way of example, by the following formula scheme:

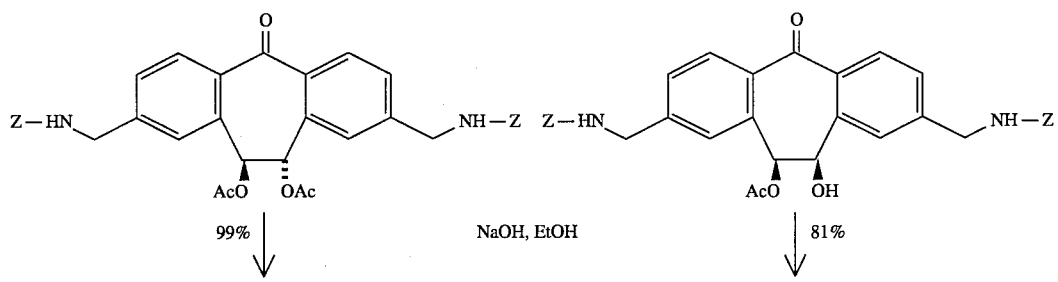

-continued

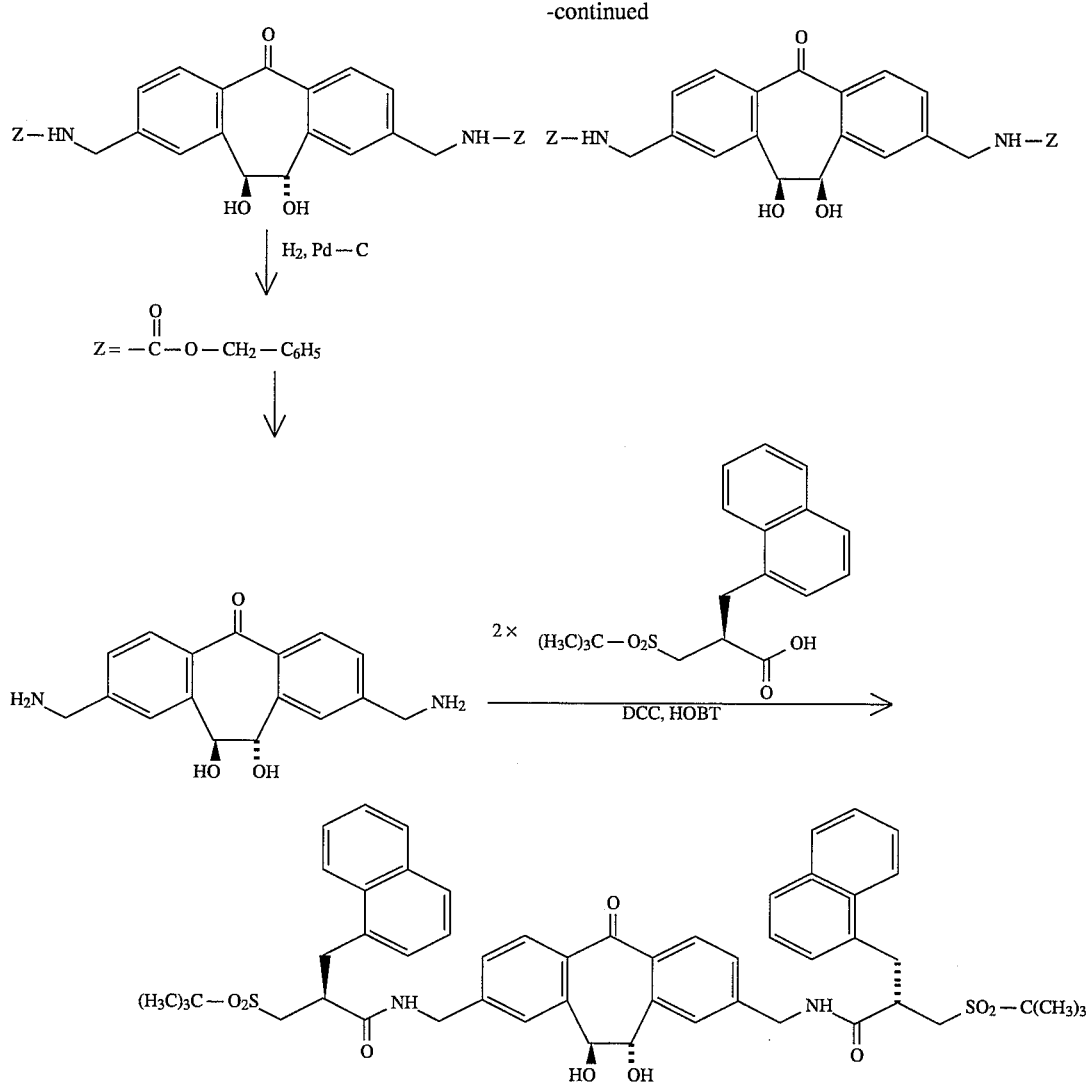

The reaction with the carboxylic acids of the general formula (IV) generally takes place within a temperature range of −20° C. to 80° C., preferably of 0° C. to +40° C., and under atmospheric pressure.

Acetic acid/silver acetate, propionic acid/silver propionate, or butyric acid/silver butyrate are in general suitable as the carboxylic acid/salt system. Acetic acid/silver acetate is preferred.

The customary inorganic bases are suitable bases for the hydrolysis. These preferably include alkali metal hydroxides or alkaline earth metal hydroxides, such as, for example, sodium hydride, potassium hydroxide or barium hydroxide, or alkali carbonates, such as sodium or potassium carbonate or sodium hydrogen carbonate. Sodium hydroxide or potassium hydroxide are particularly preferably employed.

Water, or the organic solvents which are customary for hydrolysis, are suitable solvents for the hydrolysis. These preferably include alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is likewise possible to employ mixtures of the said solvents.

The hydrolysis is generally carried out within a temperature range of 0° C. to +100° C., preferably of +20° C. to +80° C.

In general, the hydrolysis is carried out under atmospheric pressure. However, it is also possible to employ reduced pressure or elevated pressure (e.g. from 0.5 to 5 bar).

In carrying out the hydrolysis, the base is generally employed in a quantity of 1 to 3 mol, preferably of 1 to 1.5 mol, based on 1 mol of the ester. Equimolar quantities of the reactants are particularly preferably used.

The elimination of the amino-protective groups ($R^{14}/R^{15}$) takes place in a manner known per se under acidic or basic conditions, or reductively by catalytic hydrogenation, for example using Pd/C in organic solvents such as ethers, e.g. tetrahydrofuran or dioxane, or alcohols, e.g. methanol, ethanol or isopropanol.

The hydrogenation generally takes place within a temperature range of 0° C. to 80° C., preferably of 0° C. to 40° C.

In general, the hydrogenation is carried out under an elevated pressure of 2 bar to 8 bar, preferably of 3 to 5 bar.

The customary inert solvents which are not altered under the reaction conditions are suitable solvents for the reaction with the compounds of the general formula (V). These preferably include organic solvents such as ethers, e.g. diethyl ether, glycol mono- or dimethyl ether, dioxane or tetrahydrofuran, or hydrocarbons, such as benzene, toluene, xylene, cyclohexane or petroleum fractions, or halogenohydrocarbons, such as methylene chloride, chloroform, carbon tetrachloride, or dimethyl sulphoxide, dimethyl formamide, hexamethylphosphoric triamide, ethyl acetate, pyridine, triethylamine or picoline. It is likewise possible to use mixtures of the said solvents. Dichloromethane, chloroform, dimethylformamide or tetrahydrofuran are particularly preferred.

As auxiliary compounds, condensing agents are preferably employed and can also be bases, in particular if the carboxylate group is present in activated form as the anhydride. In this instance, the customary condensing agents are preferred, such as carbodiimides, e g. N,N'-diethyl-, N,N'-diisopropyl- or N,N'-dicyclohexylcarbodiimide, N-(3-dimethylaminoisopropyl)-N'-ethyl-carbodiimide hydrochloride, or N-cyclohexyl-N'-(2-morpholinoethyl)-carbodiimide metho-p-toluenesulphonate, or carbonyl compounds, such as carbonyldiimidazole, or 1,2-oxazolium compounds, such as 2-ethyl-5-phenyl-1,2-oxazolium 3-sulphate or 2-tert-butyl-5-methyl-isoxazolium perchlorate, or acylamino compounds, such as 2-ethoxy-1-ethoxy-carbonyl-1,2-dihydroquinoline, or propanephosphonic anhydride, or isobutyl chloroformate, or benzotriazolyloxytris(dimethylamino)phosphonium hexafluorophosphate, or 1,hydroxybenzotriazole.

In addition, alkali metal carbonates, e.g. sodium or potassium carbonate or sodium or potassium hydrogen carbonate, or organic bases, such as trialkylamines, e.g. triethylamine, ethyldiisopropylamine, N-ethylmorpholine, N-methylpiperidine or N-methylmorpholine can be employed, for example. N-methylmorpholine is preferred.

The auxiliary compounds and bases are employed in a quantity of 1.0 mol to 3.0 mol, preferably 1.0 to 1.2 mol, based on, in each case, 1 mol of the compounds of the general formula (V).

The reactions are carried out within a temperature range of −30° C. to 100° C., preferably at 0° C. to 30° C., and under atmospheric pressure.

The reactions can be carried out both under atmospheric pressure and under elevated or reduced pressure (for example 0.5 to 5 bar), preferably under atmospheric pressure.

The compounds of the general formulae (IV) and (V) are known or can be prepared according to customary methods.

The compounds of the general formulae (Ia) and (Ib) are novel and can be prepared as described above.

The compounds of the general formula (III) are likewise novel and can be prepared by first reacting 2,8-bis-azidomethyl-5-oxo-di-benzo[a,d]cyclohepta-1,4,6-triene of the formula (VI),

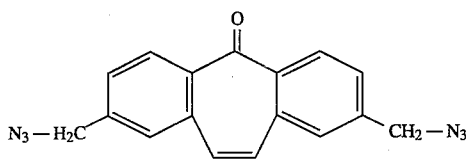

after having been taken up in ethers, preferably in THF, with triphenylphosphine/water with the formation of the diamine, and subsequently with compounds of the general formula (VIIa) or (VIIb)

 (VIIa)

 (VIIb)

in which $R^{18}$ and $R^{19}$ embrace the above-listed range of meaning for the radicals $R^{14}/R^{15}$, in inert solvents, in the presence of a base and an auxiliary compound, and, in the case of the carboxylic acids (VIIa), with prior activation of the carboxylic acid function, and, in a last step, carrying out a bromination with elemental bromine in inert solvents.

The reaction with triphenylphosphine/$H_2O$ takes place within a temperature range of 0° C. to +50° C., preferably at room temperature, and under atmospheric pressure.

The reaction with the compounds of the general formula (VII) is effected in analogy with the description, set out above, of the reaction with the compounds of the general formula (IV).

The bromination takes place in halogenohydrocarbon/glacial acetic acid mixtures, preferably dichloromethane/glacial acetic acid, and at room temperature.

The compound of the formula (VI) is likewise novel and can, for example, be prepared by first converting 2,8-dimethyl-5-oxo-dibenzo[a,d]cyclohepta-1,4,6-triene of the formula (VIII),

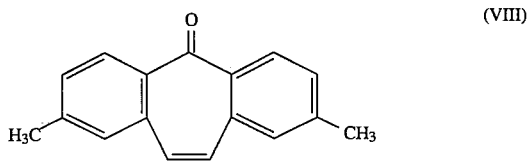

as described above, by reaction with N-bromosuccinimide in one of the above-listed solvents, preferably carbon tetrachloride, and while irradiating, into the compounds of the formula (IX)

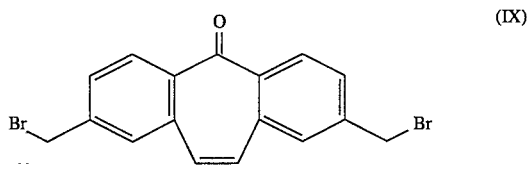

and, in a following step, reacting with lithium azide in dimethyl sulphoxide.

The bromination proceeds within a temperature range of 50° C. to +120° C. preferably of +70° C. to +100° C.

The reaction with lithium azide is generally carried out within a temperature range of 0° C. to +70° C. preferably at room temperature.

The compound of the formula (IX) is novel and is prepared as described above.

The compound of the formula (VIII) is novel and can, for example, be prepared by first converting 4-methyl-2-[2-(3-methylphenyl)ethyl]benzoic acid of the formula (X),

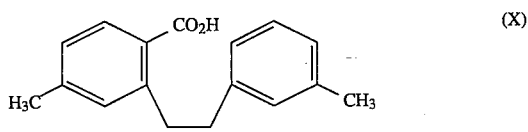

by reaction with polyphosphoric acid in sulpholane, into the compound of the formula (XI)

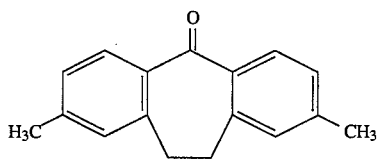

and, in a following step, as already described several times, brominating with N-bromosuccinimide in carbon tetrachloride, while irradiating, and subsequently eliminating hydrogen bromide under the influence of a base.

The reaction to give the compounds of the formula (X) proceeds within a temperature range of +20° C. to +120° C., preferably of +60° C. to +100° C., for the bromination, and +20° C. to +60° C. for the elimination.

The elimination occurs in an inert solvent, preferably dimethylformamide. Preferred bases are DBN, DBU and DABCO.

The compound of formula (XI) is novel and can be prepared as described above.

The compound of formula (X) is likewise novel and is prepared by reacting 2,4-dimethylbenzoic acid, in a LDA/THF/n-hexane solution, with 3-methylbenzyl bromide.

The reaction takes place within a temperature range of $-40°$ C. to $+40°$ C., preferably of $-30°$ C. to $+20°$ C.

The inhibitors described here are inhibitors of HIV protease and, as such, may be employed for all purposes for which enzyme inhibitors are suitable. This is, for example, their employment in diagnosis in order to improve the precision and selectivity of enzyme activity measurements. They can serve as affinity labels in affinity chromatography and can be used in research to elucidate reaction mechanisms and the specificity of enzymic reactions.

Besides this, it has been found, surprisingly, that the compounds of the general formula (I) possess an exceptionally strong effect on retroviruses. This is verified by means of an HIV-specific protease enzyme test.

The results of the examples listed below were determined according to the HIV test system described in the following references [cf. Hansen, J., Billich, S., Schulze, T., Sukrow, S. and Mölling, K (1988), EMBO Journal, Vol. 7, No. 6, pp. 1785–1791]: purified HIV protease was incubated with synthetic peptide which imitates a cleavage site in the Gag precursor protein and represents an in-vivo cleavage site for the HIV protease. The cleavage products of the synthetic peptide which resulted were analysed by means of reverse phase high performance liquid chromatography (RP-HPLC). The $IC_{50}$ values which are given refer to the substance concentrations which, under the test conditions set out above, effect a 50% inhibition of the protease activity.

TABLE 1

| Exp. No. | $IC_{50}$ (μm) |
|---|---|
| 4 | 0.005 |
| 6 | 2 |

In addition, the compounds according to the invention showed an effect in lentivirus-infected cell cultures. It was possible to demonstrate this using the HIV virus as example.
HIV infection in cell culture The HIV test was carried out, with minor modifications, according to the method of Pauwels et al. [cf. Journal of Virological Methods 20, (1988), 309–321].

Normal human blood lymphocytes (PBLs) were enriched through Ficoll-Hypaque and stimulated in RPMI 1640, 20% fetal calf serum containing phytohaemagglutinin (90 μg/ml) and interleukin-2 (40 U/ml). For infection with the infectious HIV, the PBLs were pelleted and the cell pellet was subsequently suspended in 1 ml of HIV virus adsorption solution and incubated at 37° C. for 1 hour.

The virus adsorption solution was centrifuged and the infected cell pellet was taken up in growth medium in such a way that the suspension was adjusted to $1\times10^5$ cells per ml. The cells infected in this manner were pipetted, at $1\times10^4$ cells/well, into the wells of 96-well microtitre plates.

The first vertical row of the microtitre plate contained only growth medium and cells which were not infected but which otherwise had been treated exactly as described above (cell control). The second vertical row of the microtitre plate contained only HIV-infected cells (virus control) in growth medium. The remaining wells contained the compounds according to the invention in different concentrations, starting from the wells of the 3rd vertical row of the microtitre plate, from which the substances under examination were diluted $2^{10}$-fold in doubling steps.

The test mixtures were incubated at 37° C. until the syncytium formation which is typical for HIV appeared in the untreated virus control (between day 3 and 6 after infection) and it was then evaluated microscopically. Under these test conditions, about 20 syncytia resulted in the untreated virus control while the untreated cell control contained no syncytia.

The $IC_{50}$ values were determined as the concentration of the compound according to the invention at which 50% (about 10 syncytia) of the virus-induced syncytia were suppressed by the treatment with this compound.

It has now been found that the compounds according to the invention protect HIV-infected cells from virus-induced cell destruction.

TABLE 2

| Exp. No. | $IC_{50}$ (μm) |
|---|---|
| 4 | 10 |
| 5 | 10 |

The compounds according to the invention represent valuable active compounds for the treatment and prophylaxis of diseases caused by retroviruses in human and veterinary medicine.

Ranges of indications in human medicine which may be mentioned by way of example are:

1.) The treatment and prophylaxis of human retrovirus infections.

2.) For the treatment or prophylaxis of diseases (AIDS) caused by HIV I (human immunodeficiency virus; previously termed HTLV III/LAV) and HIV II, and the stages associated therewith, such as ARC (AIDS-related complex) and LAS (lymphadenopathy syndrome), as well as the immunodeficiency and encephalopathy caused by this virus.

3.) For the treatment and prophylaxis of an HTLV-I or HTLV-II infection.

4.) For the treatment or the prophylaxis of the AIDS-carrier state.

Indications in veterinary medicine which may be listed by way of example are:

Infections with
   a) maedi-visna (in sheep and goats)
   b) progressive pneumonia virus (PPV) (in sheep and goats)

c) caprine arthritis-encephalitis virus (in sheep and goats)
d) zwoegerziekte virus (in sheep)
e) equine infectious anaemia virus
f) infections caused by the feline leukemia virus
g) infections caused by the feline immunodeficiency virus (FIV)
h) infections caused by the simian immunodeficiency virus (SIV)

Of the range of indications in human medicine, the above-listed points 2, 3 and 4 are preferred.

Pharmaceutical preparations which, besides non-toxic, inert pharmaceutically suitable excipients, contain one or more compounds of the formula (I)/(Ia)/(Ib), or which are composed of one or more active compounds of the formula (I)/(Ia)/(Ib), as well as processes for preparing these preparations, are also included in the present invention.

The active compounds of the formula (I)/(Ia)/(Ib) should preferably be present in the above-listed pharmaceutical preparations at a concentration of about 0.1 to 99.5, preferably of about 0.5 to 95, % by weight of the total mixture.

As well as the compounds of the formula (I)/(Ia)/(Ib), the above-listed pharmaceutical preparations can also contain further pharmaceutical active compounds.

The above-listed pharmaceutical preparations are prepared in a customary manner according to known methods, e.g. by mixing the active compound(s) with the excipient(s).

In order to achieve the desired results, it has in general been found advantageous both in human and in veterinary medicine to administer the active compound(s) according to the invention in total quantities of about 0.5 to about 500, preferably 1 to 100, mg/kg of body weight every 24 hours, optionally in the form of several individual doses. One individual dose preferably contains the compound(s) in quantities of about 1 to about 80, in particular 1 to 30, mg/kg of body weight. However, it can be necessary to deviate from the said dosages, specifically depending on the nature and the body weight of the subject to be treated, the nature and the severity of the disease, the type of preparation and of the administration of the pharmaceutical, as well as the period or interval within which the administration takes place.

Starting compounds

EXAMPLE I

4-Methyl-2-[2-(3-methylphenyl)ethyl]benzoic acid

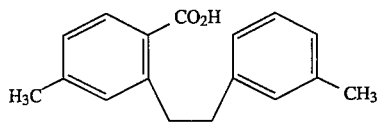

2,4-Dimethylbenzoic acid (54 g, 0.36 mol), dissolved in THF (500 ml), is added dropwise, between 10°–20° C., to a solution of LDA (0.76 mol) in THF/n-hexane (1 l/300 ml). The mixture is subsequently stirred at RT for 30 min and then cooled to −20° C. 3-Methylbenzyl bromide (80 g, 0.43 mol), in THF (300 ml), is added dropwise at this temperature. The mixture is subsequently stirred at the same temperature for 15 min, and worked up. For this, the mixture is partitioned between 2N hydrochloric acid and EtOAc, the aqueous phase is extracted with EtOAc, and the organic phases are combined, washed with saturated NaCl, dried (MgSO$_4$) and concentrated in vacuo. The residue is purified on silica gel using toluene/EtOAc 10:1 as the eluant, and the resulting product is crystallised from ether/petroleum ether.

Yield: 45.3 g (42% of theory) $^1$H-NMR (CDCl$_3$): δ=2.32 (s, 3H); 2,38 (s, 3H); 2.90 (m, 2H); 3.30 (m, 2H); 7.00–7.25 (m, 6H); 8.00 (d, J=9 Hz, 1H).

EXAMPLE II 2,8-Dimethyl-5-oxo-dibenzo[a,d]cyclohepta-1,4-diene

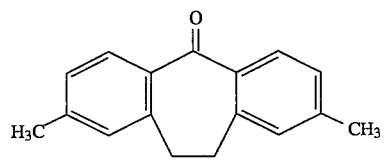

22.65 g (89 mmol) of the compound from Example I are heated in sulpholane (110 g) and polyphosphoric acid (460 g) at 110° C. for 4 h. After cooling, the solution is poured into water (2 l) and extracted three times with EtOAc, and the combined organic phases are washed with water and dried (MgSO$_4$). After evaporation in vacuo, chromatography on silica gel takes place using pure toluene as the eluant and the resulting product is crystallised from ether/petroleum ether.

Yield: 21.05 g (100% of theory) $^1$H-NMR (CDCl$_3$): δ=2.35 (s, 6H), 3.12 (s, 4H); 7.00 (s, 2H); 7.12 (d, J=8 Hz, 2H); 7.98 (d, J=8 Hz, 2H).

EXAMPLE III 2,8-Dimethyl-5-oxo-dibenzo[a,d]cyclohepta-1,4,6-triene

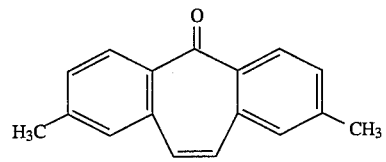

21 g (88.9 mmol) of the compound from Example II are dissolved in tetrachloromethane (450 ml) and irradiated with N-bromosuccinimide (19 g, 107 mmol) at 55° C. using a 250 W photographic lamp. After 7 h, the solution is cooled and then filtered, the filtrate is concentrated in vacuo and the residue is dissolved in DMF (70 ml). The solution is heated to 80° C. and DBN (13.25 g, 107 mmol) is added at this temperature. After 15 min, the mixture is cooled and partitioned between water and ether, the aqueous phase is extracted once with ether, and the combined organic phases are washed with 1N hydrochloric acid (3×) and water (2×), dried (MgSO$_4$) and concentrated in vacuo. The residue is crystallised from ether/petroleum ether. 11.4 g of product are obtained. A further 2.2 g of product can be obtained from the mother liquor by chromatography on silica gel using pure toluene as the eluant.

Yield: 13.6 g (65% of theory) $^1$H-NMR (CDCl$_3$) δ=2.46 (s, 6H); 6.95 (s, 2H); 7.32 (s, 2H); 7.36 (d, J=8 Hz, 2H); 8.19 (d, J=8 Hz, 2H).

EXAMPLE IV 2,8-Bis-bromomethyl-5-oxo-dibenzo[a,d]cyclohepta-1,4,6-triene

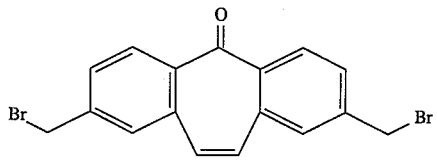

39.8 g (170 mmol) of the compound from Example III and N-bromosuccinimide are heated under reflux for about 4 h in tetrachloromethane (1.5 l) while being irradiated by a 250 W photographic lamp. The reaction is stopped when the desired dibromide can be seen, by TLC, to be the main component in the mixture of starting compound, monobromide, dibromide and by-products. Undissolved material is filtered off with suction while hot, washing with tetrachloromethane. The residue is recrystallised from dichloromethane, thereby yielding 20 g of product which is contaminated with succinimide. The first filtrate and the mother liquor from the crystallisation are combined and concentrated in vacuo, and the residue is chromatographed on silica gel using pure toluene as the eluant. 12 g of product and about 17 g of monobromo compound are obtained. This monobromo compound (17 g, 54 mmol) is reacted precisely according to the above instructions with N-bromosuccinimide (11.6 g, 65 mmol) and a further 8.6 g of the desired dibromide are obtained.

Yield: 40.6 g (65.5%) $^1$H-NMR (CDCl$_3$): δ=4.56 (s, 4H); 7.03 (s, 2H); 7.53 (s, 2H); 7.57 (d, J=8 Hz, 2H); 8.20 (d, J=8 Hz, 2H).

EXAMPLE V 2,8-Bis-azidomethyl-5-oxo-dibenzo[a,d]cyclohepta-1,4,6-triene

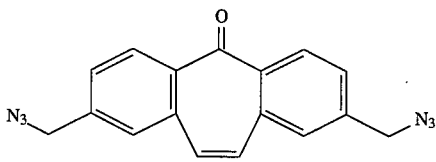

36.5 g (93 mmol) of the compound from Example IV are suspended in DMSO (250 ml) and then mixed at RT with lithium azide (13.7 g, 280 mmol). After about 10 min, the solids are completely dissolved. Working up takes place after 30 min. This is done by partitioning between EtOAc and saturated NaCl, and extracting the aqueous phase with EtOAc. The organic phases are combined, washed three times with saturated NaCl, dried (MgSO$_4$) and concentrated, but not quite to dryness, in vacuo at RT. The concentrated solution which remains is mixed with petroleum ether and the resultant solid (15.15 g) is filtered off with suction. The mother liquor is concentrated and the residue is chromatographed on silica gel using toluene/EtOAc 10:1 as the eluant. This yields a further 3.6 g of the title compound.

Yield: 18.75 g (63.5%) $^1$H-NMR (CDCl$_3$): δ=4.50 (s, 6H); 7.08 (s, 2H); 7.48 (m, 4H); 8.24 (d, J=8 Hz, 2H).

EXAMPLE VI 2,8-Bis-phenylmethoxycarbonylaminomethyl-5-oxo-dibenzo[a,d]cyclohepta-1,4,6-triene

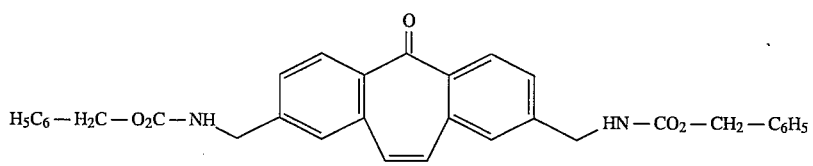

Water (45 ml) and triphenylphosphine (29.5 g, 112.3 mmol) are added to 18.75 g (51.1 mmol) of the compound from Example V in THF (700 ml) and the mixture is stirred at RT overnight. For the working up, the mixture is concentrated in vacuo, taken up in dichloromethane and the aqueous phase separated off, and the organic phase is then dried (MgSO$_4$), concentrated in vacuo and thoroughly dried under high vacuum. The crude diamine thus obtained is dissolved in dichloromethane (1 l) and, at −5° C., triethylamine (33.3 g, 330 mmol) and benzyloxycarbonyl chloride (37.5 g, 220 mmol) are successively added. Subsequently, the mixture is allowed to reach RT and is then stirred for 3.5 h. For the working up, the mixture is diluted with dichloromethane (1 l), extracted once with water and filtered with suction to remove the solid which is present, and the residue is then discarded. The aqueous phase is extracted with dichloromethane and the combined organic phases are washed with saturated NaHCO$_3$, dried (MgSO$_4$) and concentrated in vacuo to about 300 ml. The resulting jelly-like solid is filtered off with suction and the mother liquor is concentrated completely and subsequently chromatographed on silica gel using toluene/EtOAc 2:1 as the eluant. The fractions containing the product are concentrated and combined with the jelly obtained above. This residue is dissolved in hot dichloromethane/methanol 1:1, and EtOAc (200 ml) and toluene (200 ml) are added and the mixture concentrated in vacuo to about 100 ml. During this, solid which is readily filterable precipitates out, and this solid was isolated by filtration.

Yield: 11.5 g (42% of theory) $^1$H-NMR (DMSO-d$_6$): δ=4,39 (d, J=7 Hz, 4H), 5.00 (s, 4H); 7.10 (s, 2H); 7.30 (m, 10H); 7.45 (d, J=8 Hz, 2H); 7.51 (s, 2H); 7.91 (t, J=7 Hz, 2H); 8.03 (d, J=8 Hz, 2H).

EXAMPLE VII 2,8-Bis-phenylmethoxycarbonylaminomethyl-10,11-dibromo-5-oxo-dibenzo[a,d]cyclohepta-1,4-diene

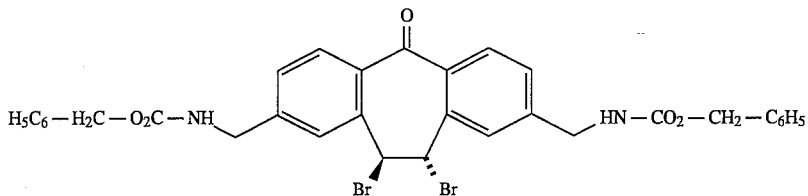

10 g (18.8 mmol) of the compound from Example VI and bromine (6g, 38 mmol) are stirred overnight in dichloromethane (600 ml) and glacial acetic acid (200 ml) with the exclusion of light. The mixture is then concentrated in vacuo and the residue is chromatographed on silica gel using toluene/EtOAc/formic acid 5:1:0.02.

Yield: 11.0 g (84.5% of theory) $^1$H-NMR (DMSO-$d_6$): δ=4.30 (d, J=7Hz, 4H); 5.08 (s, 4H); 6.12 (s, 2H); 7.35 (m, 12H); 7.95 (m, 4H).

Preparation examples

EXAMPLE 1, EXAMPLE 2 and EXAMPLE 3

(trans)-2,8-Bis-phenylmethoxycarbonylaminomethyl-10,11-diacetoxy-5-oxo-dibenzo[a,d]cyclohepta-1,4-diene silver acetate (1.77 g, 10.6 mmol) are maintained under reflux for 3 h in dry acetic acid (100 ml, prepared by heating 150 ml of acetic acid and 10 ml of acetic anhydride under reflux for 1 h). Subsequently, the mixture is cooled and filtered to remove solid, and the filtrate is concentrated in vacuo. The residue is chromatographed on silica gel using toluene/ethyl acetate 2:1 as the eluant. This results in the elution of the trans compound (Example 1). Subsequently, the cis component (Example 2) is eluted using ethyl acetate/acetone 1:1.

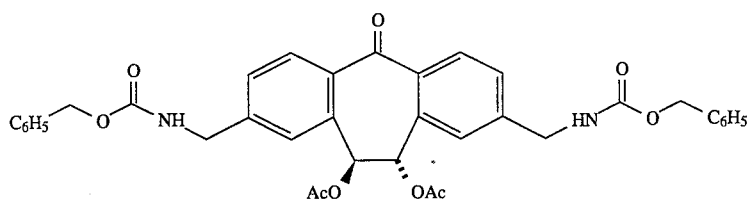

(1)

(cis)-10-Acetoxy-2,8-bis-phenylmethoxycarbonylaminomethyl-11-hydroxy-5-oxo-dibenzo[a,d]cyclohepta-1,4-diene

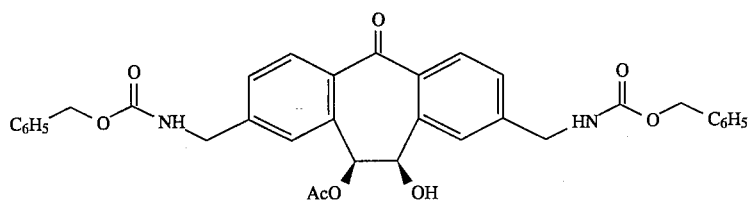

(2)

(cis)-11-Acetoxy-5-hydroxy-2,8-bis-phenylmethoxycarbonylaminomethyl-dibenzo[b,e]bicyclo[2.1.3]1-oxaoctane

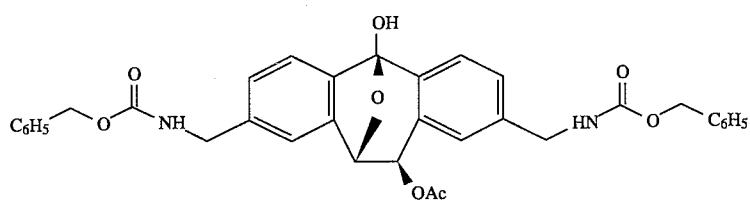

(3)

2.44 g (3.53 mmol) of the compound from Example VII and

EXAMPLE 1

Yield: 1.57 g (68.5% of theory) $^1$H-NMR (DMSO-$d_6$): δ=1.82 (s, 6H); 4.28 (d, J=7 Hz, 4H); 5.05 (s, 4H); 6.21 (s, 2H); 7.35 (m, 14H), 7.82 (d, J=8 Hz, 2H); 7.95 (t, J=7Hz, 2H).

EXAMPLE 2

Yield: 0.43 g (20% of theory) $^1$H-NMR (DMSO-$d_6$): δ=2.02 (s, 3H); 4.29 (d, J=7 Hz, 4H); 5.06 (m, 5H); 6.12 (s, 1H); 6.19 (d, J=5 Hz, 1H); 7.31 (m, 13H); 7.50 (s, 1H); 7.73 (d, J=8 Hz, 1H); 7.79 (d, J=8 Hz, 1H); 7.96 (t, J=7 Hz, 2H).

As well as 89% of the compound from Example 2, 11% of the compound from Example 3, which is in equilibrium with Example 2, is also seen in the $^1$H-NMR. Characteristic signals: $^1$H-NMR (DMSO-d6): δ=4.10 (d, J=2 Hz, 2H); 4.19 (d, J=7 Hz, 2H); 5.42 (s, 1H); 7.00–7.25 (m, 6H).

EXAMPLE 4

(trans)-2,8-Bis-phenylmethoxycarbonylaminomethyl-10,11-dihydroxy-5-oxo-dibenzo[a,d]cyclohepta-1,4-diene

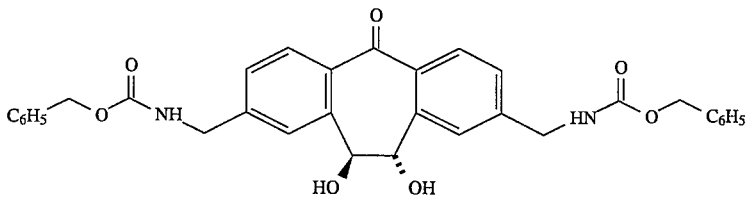

0.1N NaOH (126 ml) is added to 1.8 g (2.76 mmol) of the compound from Example 1 in ethanol (180 ml) and the mixture is stirred at RT for 1 h. Subsequently, the alcohol is evaporated off in vacuo and the aqueous phase is extracted three times with EtOAc. The organic phases are combined, washed with saturated NaCl, dried (MgSO$_4$) and concentrated in vacuo. The residue is stirred with dichloromethane, and the resulting solid (1.38 g) is filtered off with suction. The mother liquor is concentrated and chromatographed on silica gel using toluene/ethyl acetate 1:1, then 1:2, as the eluant. This yields a further 0.18 g of product.

MS (FAB): 567 (M$^+$+H, 100%) $^1$H-NMR (DMSO-$d_6$): δ=4.26 (d, J=7 Hz, 4H); 4.86 (m, 2H); 5.08 (s, 4H); 5.82 (m, 2H); 7.23 (d, J=8 Hz, 2H); 7.25 (s, 2H); 7.32 (s, 10H); 7.65 (d, J=8 Hz, 2H); 7.93 (t, J=7 Hz, 2H).

As well as 94% of the compound from Example 4, 6% of the isomeric hemiacetal is also seen in analogy with Example 3 in the $^1$H-NMR. Characteristic signals: $^1$H-NMR (DMSO-$d_6$): δ=4.10 (d, J=7 Hz, 2H); 4.17 (dm, J=7 Hz, 2H); 5.02 (m, 1H); 5.22 (d, J=6 Hz, 1H); 5.76 (d, J=5 Hz, 1H); 7.80 (s, 1H, OH).

EXAMPLE 5

(cis)-2,8-Bis-phenylmethoxycarbonylaminomethyl-10,11-dihydroxy-5-oxo-dibenzo[a,d]cyclohepta-1,4-diene

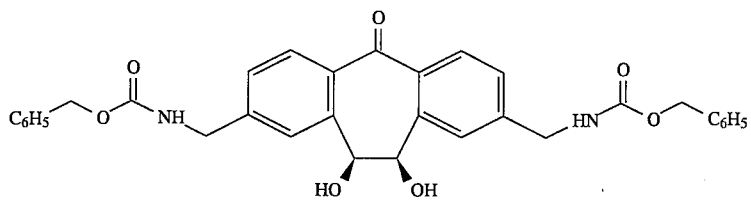

The compound is prepared from the compound of Example 2 in analogy with the instructions in Example 4.

Yield: 81% $^1$H-NMR (DMSO-$d_6$): δ=4.28 (d, J=7 Hz, 4H); 4.89 (d, J=6 Hz, 2H); 5.07 (s, 4H); 5.70 (d, J=6 Hz, 2H); 7.23 (d, J=8 Hz, 2H); 7.32 (s, 10H); 7.50 (s, 2H); 7.73 (d, J=8 Hz, 2H); 7.94 (t, J=7 Hz, 2H).

As well as 91% of the compound from Example 4, 9% of the isomeric hemiacetal is also seen in analogy with Example 3 in the $^1$H-NMR. Characteristic signals: $^1$H-NMR (DMSO-$d_6$): δ=4.10 (d, J=7 Hz, 2H); 4.17 (d, J=7 Hz, 2H); 5.02 (m, 1H); 5.28 (s, 1H); 7.86 (s, 1H, OH).

EXAMPLE 6

(trans)-10,11-Dihydroxy-2,8-bis-[5,5-dimethyl-4,4-dioxo-2-(1-naphthylmethyl)-4-thiahexanoylaminomethyl-5-oxodibenzo[a,d]cyclohepta-1,4-diene

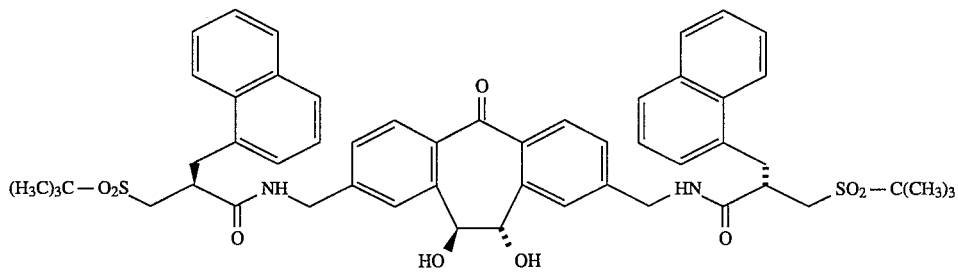

200 mg (0.35 mmol) of the compound from Example 4 are hydrogenated under 1 bar in methanol (100 ml) and in the presence of 10% Pd/C (40 mg) for 3.5 h. Subsequently, the mixture is filtered to remove the catalyst, and the filtrate is concentrated in vacuo. HOBT (95 mg, 0.70 mmol) and DCC (160 mg, 0.78 mmol) are added to 5,5-dimethyl-4,4-dioxo-2-(1-naphthylmethyl)-4-thiahexanoic acid (235 mg, 0.70 mmol) in THF (4 ml), while cooling with ice. The mixture is subsequently stirred at RT for 1 h and then added to the crude diamine (obtained above by hydrogenation) in dichloromethane (2 ml). The mixture is subsequently stirred at RT for 5 h and then diluted with EtOAc (150 ml). The solution is washed with 4% strength acetic acid (25 ml), saturated NaHCO₃, and saturated NaCl, and then dried (MgSO₄) and concentrated in vacuo. The residue is purified on silica gel using EtOAc/acetone 5:1, and then 5:2. A jelly-like product is obtained which is thoroughly triturated with dichloromethane to achieve crystallisation. Further product can be obtained from the mother liquor by dissolving in acetone/methanol, adding ether and crystallising in a refrigerator.

Yield: 46 mg (14% of theory) $^1$H-NMR (DMSO-$d_6$): δ=1,24 (s, 9H); 3.10 (dd, J=14 Hz and 3 Hz, 2H); 3.35 (m, 6H); 3.59 (dd, J=14 Hz and 6 Hz, 2H); 4.16 (dd, J=16 and 5 Hz, 2H); 4.30 (dd, J=16 Hz and 5 Hz, 2H), 4.82 (m, 2H); 5.71 (m, 2H); 6.88 (d, J=8 Hz, 2H); 7.21 (s, 2H); 7.30–7.60 (m, 10H), 7.83 (d, J=8 Hz, 2H); 7.95 (d, J=8 Hz, 2H); 8.24 (d, J=7 Hz, 2H); 8.64 (t, J=5 Hz, 2H).

The compounds listed in Table 1 are prepared in analogy with the instructions in Example 6:

TABLE 1

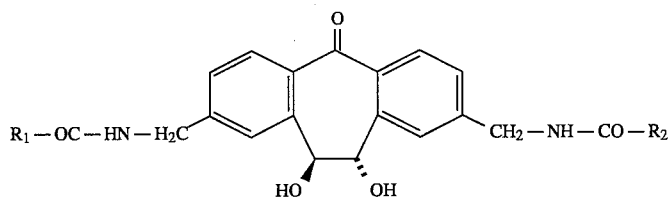

| Example no. | R¹ | R² | Yield (% of theory) |
|---|---|---|---|
| 7 |  |  | 9 |
| 8 | 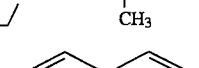 | 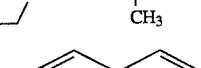 | 15 |
| 9 | 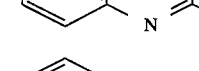 | 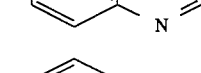 | 32 |
| 10 | C₆H₅—CH₂—O— | CH₃— | 47 |

EXAMPLE 11

(trans)-10,11-Bis-(tert-butyldimethylsilyloxy)-2,8-bis-phenylmethoxycarbonylaminomethyl-5-oxo-dibenzo[a,d]cyclo-hepta-1,4-diene

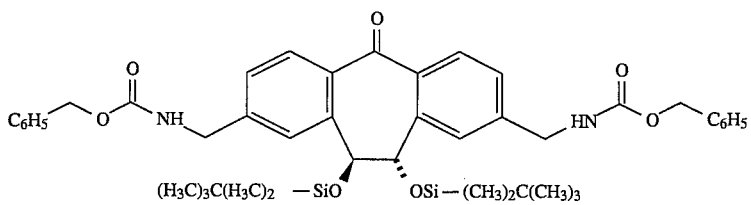

0

Imidazole (1.9 g, 28.4 mmol) and tert-butyldimethylsilyl chloride (2.35 g, 15.6 mmol) are added at RT to 4 g (7.1 mmol) of the compound from Example 4 and the mixture is then stirred at 50° C. for 2.5 h. For the working up, the mixture is diluted with EtOAc, washed with water, twice with 1N hydrochloric acid and then with saturated NaCl, and subsequently dried (MgSO$_4$) and concentrated in vacuo. The residue is purified on silica gel using toluene/EtOAc 10:1 as the eluant.

Yield: 5.1 g (90.5% of theory) $^1$H-NMR (CDCl$_3$): δ=0.19 (s, 6H), 0.07 (s, 6H); 0.61 (s, 18H), 4.42 (d, J=6 Hz, 4H); 4.93 (s, 2H); 5.04 (t, br, J=6 Hz, 2H); 5.15 (s, 4H); 7.15 (s, 2H); 7.24 (m, 2H); 7.35 (m, 10H); 7.89 (d, J=8 Hz, 2H).

EXAMPLE 12

(trans)-10,11-Dihydroxy-2,8-bis-[methyl(phenyl-methoxycarbonyl)amino]methyl-5-oxo-dibenzo[a,d]cyclohepta-1,4,6triene

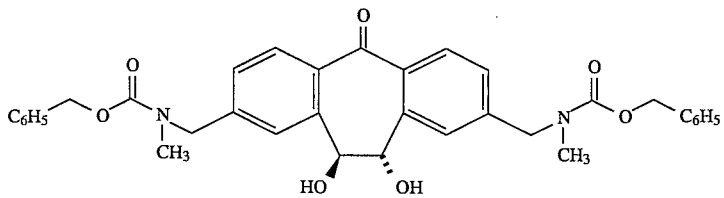

0

A 35% potassium hydride suspension (11.3 mg, 0.283 mmol) and methyl iodide (48 mg, 0.34 mmol) are added to 90 mg (0.113 mmol) of the compound from Example 11 in DMF (9 ml), while cooling with ice. After 15 min at the same temperature, working up is carried out. The mixture is partitioned between EtOAc and 1N hydrochloric acid, the aqueous phase is extracted with EtOAc, and the combined organic phases are then washed with saturated NaCl, dried (MgSO$_4$) and concentrated in vacuo. The residue is purified on silica gel using toluene/EtOAc 10:1 as the eluant. 48 mg of an intermediate are obtained whose silyl protective groups are removed in accordance with a general method for removing silyl groups (n-Bu$_4$NF, THF, RT).

Yield: 22 mg (33% of theory) $^1$H-NMR (CDCl$_3$): δ=3.86 and 3.92 (2s, 6H), 4.52 (s, 4H); 4.90 (br, 2H); 5.17 (s, 4H); 7.20–7.40 (m, 14H); 7.46 and 7.58 (2br, 2H); 7.84 (d, J=8 Hz, 2H).

We claim:

1. A 5-oxo-dibenzo(a,d)cyclohepta-1,4-diene of the formula

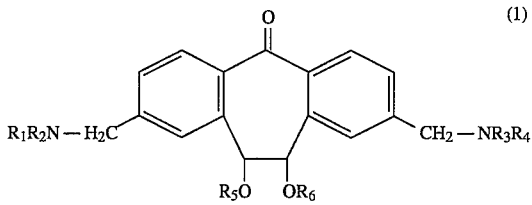

in which

R$^1$ and R$^3$ are identical or different and represent an amino-protective group or represent a group of the formula R$^7$—CO—, in which R$^7$ denotes hydrogen, trifluoromethyl, or straight-chain or branched alkoxy having up to 8 carbon atoms or alkyl having up to 18 carbon atoms which is unsubstituted or substituted identically or differently up to 2 times by aryl having 6 to 10 carbon atoms or pyridyl, or denotes aryl having 6 to 10 carbon atoms, which is unsubstitued or substituted by halogen, trifluoromethyl, trifluoromethoxy, or straight-chain or branched alkyl having up to 8 carbon atoms, denotes cycloalkyl having 3 to 7 carbon atoms, or denotes quinolyl, quinolyl N-oxide, indolyl, pyridyl, morpholino or piperazinyl, or denotes a radical of the formula

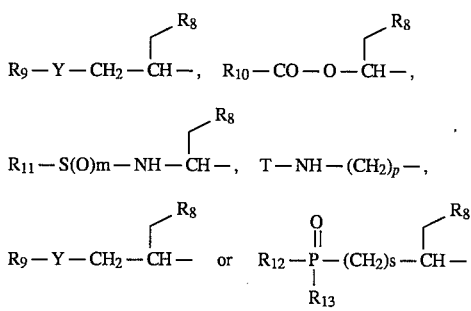

in which

R$^8$ denotes phenyl or naphthyl,

R$^9$, R$^{10}$ and R$^{11}$, independently of each other, denote straight-chain or branched alkyl having up to 14 carbon atoms, which is unsubstituted or substituted by phenyl or naphthyl, or denote aryl having 6 to 10 carbon atoms, which is unsubstituted or substituted by alkyl having up to 4 carbon atoms, or $R^{10}$ denotes a radical of the formula

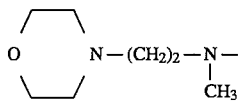

m denotes a number 0, 1, or 2,

T denotes morpholino or cyclohexyl,

P denotes a number 1, 2, or 3,

Y and Y', independently of each other, represent CO— or $SO_2$—, $R^{12}$ and $R^{13}$, independently of each other, represent hydroxyl or alkoxy having up to 8 carbon atoms, s represents a number 1 or 2, $R^2$ and $R^4$ are identical or different and represent hydrogen, or straight-chain or branched alkyl having up to 8 carbon atoms, and $R^5$ and $R^6$ are identical or different and represent hydrogen, or represent straight-chain or branched acyl or alkoxycarbonyl having in each case up to 8 carbon atoms, or represent a hydroxyl-protective group, or in case either $R^5$ or $R^6$ represents hydrogen, a hemiacetal or salt thereof.

2. A compound according to claim 1, in which $R^1$ and $R^3$ are identical or different and represent benzyloxycarbonyl, 4-methoxybenzyloxy-carbonyl, 4-nitrobenzyloxycarbonyl, tert-butoxycarbonyl, allyoxycarbonyl, 2-nitrobenzyloxycarbonyl, fluorenyl-9-methoxycarbonyl or 2,2,2-trifluoroacetyl, or represent a group of the formula $R^7$—CO—, $R^7$ denotes hydrogen, trifluoromethyl, or straight-chain or branched alkoxy having up to 4 carbon atoms or alkyl having up to 16 carbon atoms, which are unsubstituted or substituted identically or differently up to 2 times by phenyl, naphthyl or pyridyl, or denotes phenyl or naphthyl, which is unsubstituted or substituted by fluorine, chlorine, trifluoromethyl, triflouromethoxy, or by straight-chain or branched alkyl having up to 6 carbon atoms, denotes cyclopropyl, cyclopentyl, cyclohexyl, quinolyl, quinolyl N-oxide, indolyl, pyridyl, morpholino or piperazinyl, or denotes a radical of the formula

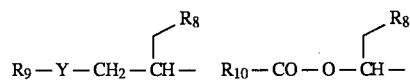

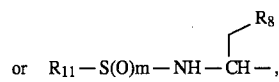

$R^{10}$ denotes a radical of the formula

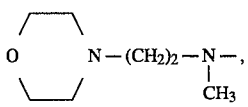

m denotes a number 1 or 2, $R^2$ and $R^4$ are identical or different and represent hydrogen, or straight-chain or branched alkyl having up to 6 carbon atoms, and $R^5$ and $R^6$ are identical or different and represent hydrogen, or represent straight-chain or branched acyl or alkoxycarbonyl having in each case up to 6 carbon atoms or represent trimethylsilyl, triethylsilyl, triisopropylsilyl, tert-butyl-dimethylsilyl, triphenylsilyl, benzyloxycarbonyl, 4-nitrobenzyloxycarbonyl, tert-butoxycarbonyl, allyloxycarbonyl, 4-benzyloxycarbonyl, formyl, acetyl or trichloroacetyl, or in case either $R^5$ or $R^6$ represents hydrogen, a hemiacetal or salt thereof.

3. A compound according to claim 1, in which $R^1$ and $R^3$ are identical or different and represent benzyloxycarbonyl, 4-methoxybenzyloxy, carbonyl, 4-nitrobenzyloxycarbonyl, tert-butoxycarbonyl, allyloxycarbonyl, 2-nitrobenzyloxycarbonyl, fluorenyl-9-methoxycarbonyl or 2,2,2-trifluoroacetyl, or represent a group of the formula $R^7$—CO—in which $R^7$ denotes hydrogen, trifluoromethyl, or straight-chain or branched alkoxy having up to 4 and alkyl having up to 14 carbon atoms, which are unsubstituted or substituted up to 2 times by phenyl, naphthyl or pyridyl, or denotes phenyl or naphthyl, which is unsubstituted or substituted by fluorine, chlorine, trifluoromethyl, trifluoromethoxy, or by straight-chain or branched alkyl having up to 4 carbon atoms, denotes cyclopropyl, cyclopentyl, cyclohexyl, quinolyl, quinolyl N-oxide, indolyl, pyridyl, morpholino or piperazinyl, or denotes a radical of the formula

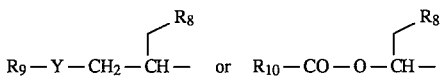

in which

Y denotes the CO and SO2 group $R^8$ denotes phenyl or naphthyl, $R^9$ and $R^{10}$ independently of each other, represent straight-chain or branched alkyl having up to 4 carbon atoms, tolyl, phenyl or naphthyl, $R^{10}$ represents a radical of the formula,

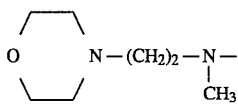

$R^2$ and $R^4$ are identical or different and represent hydrogen, or straight-chain or branched alkyl having up to 4 carbon atoms, $R^5$ and $R^6$ are identical or different and represent hydrogen, or represent straight-chain or branched acyl or alkoxycarbonyl having in each case up to 4 carbon atoms, or represent trimethylsilyl, trethylsilyl, or in case either $R^5$ or $R^6$ represents hydrogen, a hemiacetal or salt thereof.

4. A process for preparing a compound according to claim 1, which comprises reacting a compound of the formula (III)

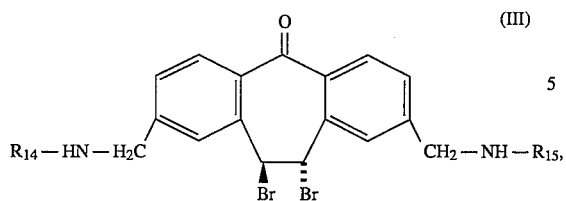 (III)

in which
  $R^{14}$ and $R^{15}$ are identical or different and represent an amino-protective group, with a carboxylic acid of the formula (IV)

$$R^{16}-CO_2H \quad (IV)$$

in which
  $R^{16}$ includes the respective range of meanings for the substituents $R^5$ and $R^6$, with the exception of hydrogen, and in the presence of a corresponding salt, thereby to form the compounds of the formulae (Ia) and (Ib)

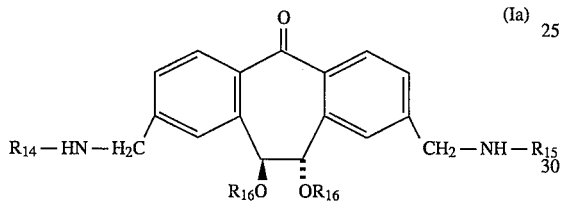 (Ia)

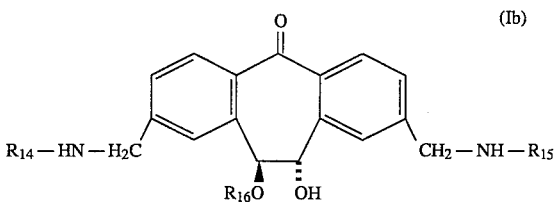 (Ib)

hydidyzing to convert R5 and R6 to hydrogen, and when $R^1$ and $R^3$ are other than hydrogen eliminating the radicals $R^{14}$ and $R^{15}$ to liberate the amino function, and reacting it in an inent solvent with a compound of the formula:

$$R^{17}-COOH \quad (V)$$

in which
  $R^{17}$ has any meaning for $R^1$ or R3.

5. A composition for combating retroviral agents comprising an amount effective therefor of a compound according to claim 4 and a pharmaceutically acceptable diluent.

6. A method of combating a retroviral agent in a patient in need thereof which comprises administering to such patient an amount effective therefor of a compound according to claim 1.

* * * * *

UNITED STATES PATENT AND TRADEMARK OFFICE
CERTIFICATE OF CORRECTION

PATENT NO. : 5,457,108
DATED : October 10, 1995
INVENTOR(S) : Wild, et al.

It is certified that error appears in the above-indentified patent and that said Letters Patent is hereby corrected as shown below:

Title Page,      item [54]: Delete " [A,DI] " and substitute -- [A,D] --

Col. 26, line 10    Delete " 4-benzyloxycarbonyl " and substitute -- 4-methoxy-benzyloxycarbonyl --

Signed and Sealed this

Twenty-third Day of January, 1996

Attest:

BRUCE LEHMAN

*Attesting Officer*     *Commissioner of Patents and Trademarks*